United States Patent
Tang et al.

(10) Patent No.: US 7,842,813 B2
(45) Date of Patent: Nov. 30, 2010

(54) PROCESSES FOR THE PREPARATION OF O-[5-(4-AMINO-THIAZOL-2-YL)-PYRIDIN-2-YLMETHYL]-HYDROXYLAMINE

(75) Inventors: Datong Tang, Newton, MA (US); Yinglin Han, Burlingame, CA (US); Yanhe Huang, Hockessin, DE (US); Ly Tam Phan, Quincy, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 12/437,636

(22) Filed: May 8, 2009

(65) Prior Publication Data

US 2009/0281324 A1    Nov. 12, 2009

Related U.S. Application Data

(60) Provisional application No. 61/095,111, filed on Sep. 8, 2008, provisional application No. 61/051,875, filed on May 9, 2008.

(51) Int. Cl.
    *C07D 417/04*    (2006.01)
(52) U.S. Cl. .................................. 546/270.4
(58) Field of Classification Search ............... 546/270.4
    See application file for complete search history.

(56) References Cited

U.S. PATENT DOCUMENTS

| 6,878,691 | B2 | 4/2005 | Or et al. |
|---|---|---|---|
| 7,022,679 | B2 | 4/2006 | Kim et al. |
| 7,064,110 | B2 | 6/2006 | Or et al. |
| 7,129,221 | B2 | 10/2006 | Or et al. |
| 7,135,573 | B2 | 11/2006 | Kim et al. |
| 7,189,704 | B2 | 3/2007 | Niu et al. |
| 7,273,853 | B2 | 9/2007 | Or et al. |
| 7,384,922 | B2 | 6/2008 | Wang et al. |
| 7,563,877 | B2 | 7/2009 | Xu et al. |
| 2006/0069139 | A1 | 3/2006 | Assaf et al. |
| 2006/0247440 | A1 | 11/2006 | Tang et al. |
| 2006/0252710 | A1 | 11/2006 | Wang et al. |
| 2007/0207972 | A1 | 9/2007 | Xu et al. |
| 2008/0242865 | A1 | 10/2008 | Tang et al. |
| 2009/0075915 | A1 | 3/2009 | Kim et al. |
| 2009/0118506 | A1 | 5/2009 | Kim et al. |
| 2009/0264380 | A1 | 10/2009 | Kim et al. |
| 2009/0270457 | A1 | 10/2009 | Kim et al. |

OTHER PUBLICATIONS

Bagley, et. al., "Total Synthesis of the Thiopeptide Promothiocin A", Casreact Abstract 133:4967, 2000.*
International Search Report for PCT/US09/43228, dated Jun. 14, 2009.

* cited by examiner

*Primary Examiner*—Janet L Andres
*Assistant Examiner*—Binta M Robinson
(74) *Attorney, Agent, or Firm*—Edgar W. Harlan; Carolyn S. Elmore; Elmore Patent Law Group, P.C.

(57) ABSTRACT

The present invention relates generally to novel methods for the synthesis of O-[5-(4-amino-thiazol-2-yl)-pyridin-2-ylmethyl]-hydroxylamine which is an essential reagent in the synthesis of one of the bridged erythromycin derivatives and their respective pharmaceutically acceptable salts in PCT Application WO 03/097659 A1. In particular, the present invention relates to processes and intermediates for the preparation of a compound of formula (Ia):

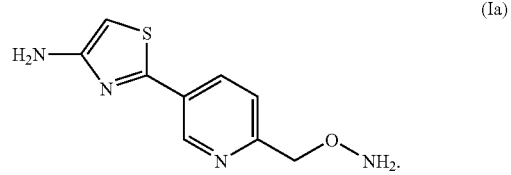

(Ia)

12 Claims, No Drawings

PROCESSES FOR THE PREPARATION OF O-[5-(4-AMINO-THIAZOL-2-YL)-PYRIDIN-2-YLMETHYL]-HYDROXYLAMINE

RELATED APPLICATIONS

This application claims the benefit of U.S. Provisional Application No. 61/051,875, filed on May 9, 2008 and U.S. Provisional Application No. 61/095,111, filed on Sep. 8, 2008. The entire teachings of the above applications are incorporated herein by reference.

TECHNICAL FIELD

The present invention relates generally to the processes and intermediates useful in the preparation O-[5-(4-Amino-thiazol-2-yl)-pyridin-2-ylmethyl]-hydroxylamine which is a reagent in the synthesis of certain bridged erythromycin and ketolide derivatives described in U.S. Pat. No. 6,878,691, U.S. Patent Pub. No. 2005037982 and PCT Application WO 03/097659 A1.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

Recently PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides methods for preparing compounds of Formula I:

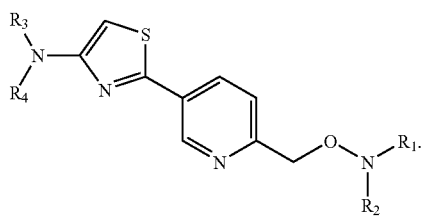

A most preferred embodiment of a compound of formula I is O-[5-(4-amino-thiazol-2-yl)-pyridin-2-ylmethyl]-hydroxylamine having the formula Ia:

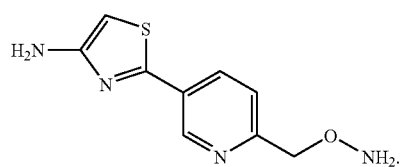

In one embodiment of the invention, pyridyl derivatives of formulae I are reacted with aminothiazole derivatives in the presence metallic catalysts. The invention further relates to increasing product yield and decreasing process steps for intermediate and large scale production O-[5-(4-amino-thiazol-2-yl)-pyridin-2-ylmethyl]-hydroxylamine. Compounds of Formula I and particularly, O-[5-(4-amino-thiazol-2-yl)-pyridin-2-ylmethyl]-hydroxylamine, are particularly useful as a reagent in the synthesis of EP16322 which has the following formula:

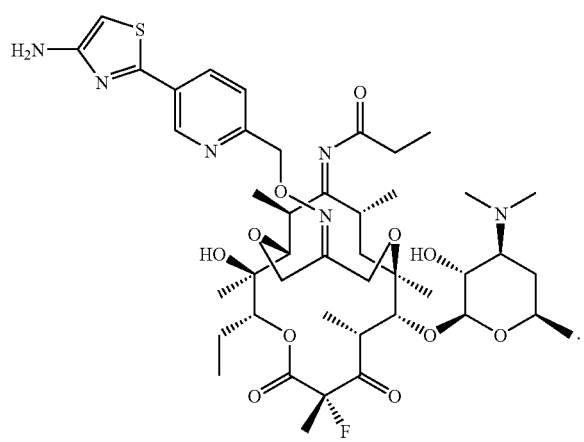

DETAILED DESCRIPTION OF THE INVENTION

In a first embodiment, the present invention provides a process for the preparation of compounds of formulae (I);

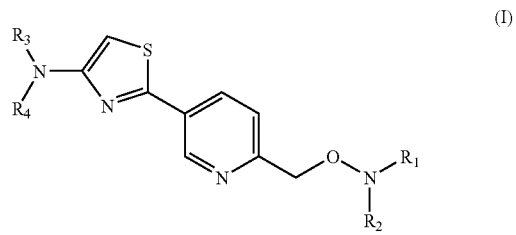

wherein $R_1$, $R_2$, $R_3$ and $R_4$ are each independently selected from:
(a) hydrogen; or
(b) $NH_2$;

or one of $R_1/R_2$ and/or one of $R_3/R_4$ is a hydrogen and the other of $R_1/R_2$ and/or the other of $R_3/R_4$ is selected from:

(a) C(O)R$_5$, where R$_5$ is C$_1$-C$_6$ alkyl, optionally substituted with one or more substituents selected from aryl, substituted aryl, heteroaryl, or substituted heteroaryl;

(b) C(O)OR$_5$, where R$_5$ is as previously defined;

alternatively, R$_1$,R$_2$ and/or R$_3$,R$_4$ are taken together with the nitrogen atom to which they are attached to form (a)

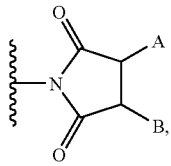

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group; or A and B taken together with the carbon to which they are attached form a cyclic moiety selected from: aryl, substituted aryl, heterocyclic, substituted heterocyclic, alicyclic, or substituted alicyclic;

b) N═C(R$_6$)(R$_7$), where R$_6$ and R$_7$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;

said process comprising one or more of the following steps:

(1) halogenating 6-hydroxymethyl-nicotinic acid methyl ester (III) with a chlorinating reagent to form compounds of formulae (IV):

(IV)

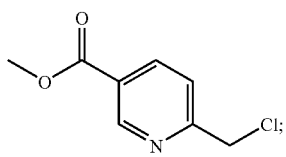

(2) treating compound (IV) with compounds of formula R$_1$R$_2$NOH wherein R$_1$ and R$_2$ are as previously defined in the presence of base to yield compounds of formulae (V):

(V)

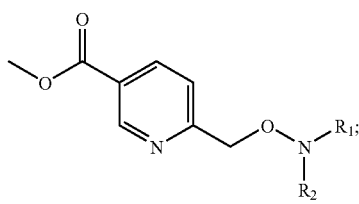

(3) reacting compound of formulae (V) with liquid ammonia or ammonia hydroxide to provide compound of formula (VI);

(VI)

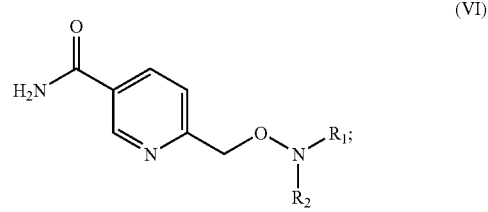

(4) reacting compound of formulae (VI) with a thionating reagent to provide compound of formula (VII);

(VII)

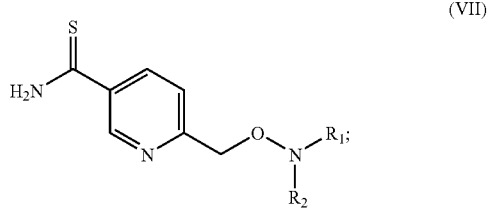

(5) reacting compound of formulae (VII) with XCH$_2$CONR$_3$R$_4$, where X is a leaving group, to provide a compound of formula (I);

(I)

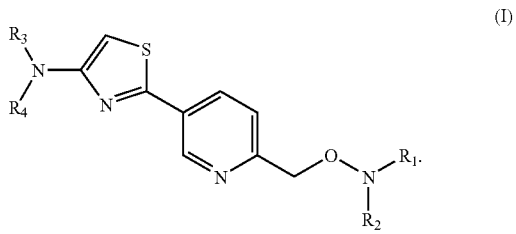

Optionally, the process may further comprise the step of hydrolyzing the compound of formula I with a base or an acid in a protogenic organic solvent or aqueous solution, to yield a preferred compound of the invention, O-[5-(4-amino-thiazol-2-yl)-pyridin-2-ylmethyl]-hydroxylamine, having the formulae (Ia):

(Ia)

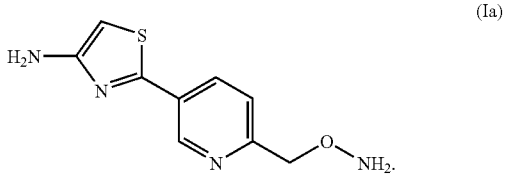

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable aliphatic or aromatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$-$C_{12}$ alkenyl" or "$C_2$-$C_6$ alkenyl" group as previously defined, substituted by one, two, three or more aliphatic substituents.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by one, two, three or more aliphatic substituents.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl or aromatic group substituted by one, two, three or more aromatic substituents.

The term "arylalkyl," as used herein, refers to an aryl group attached to the parent compound via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo [2.2.2]octyl.

The term "substituted alicyclic," as used herein, refers to an alicyclic group substituted by one, two, three or more aliphatic substituents.

The term "heterocyclic," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more aliphatic substituents.

The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "alkylamino" refers to a group having the structure —NH($C_1$-$C_{12}$ alkyl).

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, NHC(O)($C_1$-$C_{12}$ alkyl), N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al, Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "oxidizing agent(s)," as used herein, refers to reagents useful for oxidizing the 3-hydroxyl of the macrolide ring to the 3-carbonyl. Oxidizing agents suitable in the present process are either Swern oxidation reagents (dimethyl sulfoxide and an electrophilic compound selected from dicyclohexylcarbodiimide, acetic anhydride, trifluoroacetic anhydride, oxalyl chloride, or sulfur trioxide), Dess Martin oxidation reagents, or Corey-Kim oxidation reagents. A preferred method of oxidation is the use of the Corey-Kim oxidation reagents N-chlorosuccinimide-dimethyl sulfide complex.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Prodrugs include compounds wherein an amino acid residue, or a polypeptide chain of two or more (e.g., two, three or four) amino acid residues is covalently joined through an amide or ester bond to a free amino, hydroxy or carboxylic acid group of a bridged erythromycin or ketolide derivative synthesized using the reagents prepared in accordance with the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Suitable concentrations of reactants used in the synthesis processes of the invention are 0.01M to 10M, typically 01M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres include, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which may be used in the descriptions of the scheme and the examples that follow are:
Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane or 1,4-bis(diphenylphosphino)butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
HPLC for high-pressure liquid chromatography;
MeOH for methanol;
$NaN(TMS)_2$ for sodium bis(trimethylsilyl)amide;
NMMO for N-methylmorpholine N-oxide;
Rp for hydroxyl protecting group;
TEA for triethylamine;
THF for tetrahydrofuran;

TPP or PPh₃ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate (II);
TBS for tert-butyl dimethylsilyl; or
TMS for trimethylsilyl.

All other abbreviations used herein, which are not specifically delineated above, shall be accorded the meaning which one of ordinary skill in the art would attach.

Synthetic Schemes

The present invention will be better understood in connection with Schemes 1-3. It will be readily apparent to one of ordinary skill in the art that the process of the present invention can be practiced by substitution of the appropriate reactants and that the order of the steps themselves can be varied.

As outlined in Scheme 1, Step A, dimethylpyridine-2,5-dicarboxylate (II) is prepared by double methylation from pyridine-2,5-dicarboxylic acid (1-1). The present conversion preferably takes place in the presence of an acid in methanol.

A compound of formula (III) is prepared, as illustrated in Step B of Scheme 1, by selectively reducing 2-methyl ester in compound (II) with a reducing agent in the presence of an inorganic salt, such as calcium (II) salt or other metal derivatives, in organic solvent, preferably in a mixed solvent. In a preferred embodiment of the reaction, the reaction temperature is between −10° C. and 10° C. and the duration of the reaction is 1 to 24 hours. In a particularly preferred embodiment of the reaction, the reducing agent is sodium borohydride, the inorganic salt is calcium chloride and the solvent is a mixture of tetrahydrofuran, methanol and methylene chloride.

As outlined in Scheme 1, Step C, a compound of Formula (IV) is prepared by reacting of compound (III) with a chlorinating reagent.

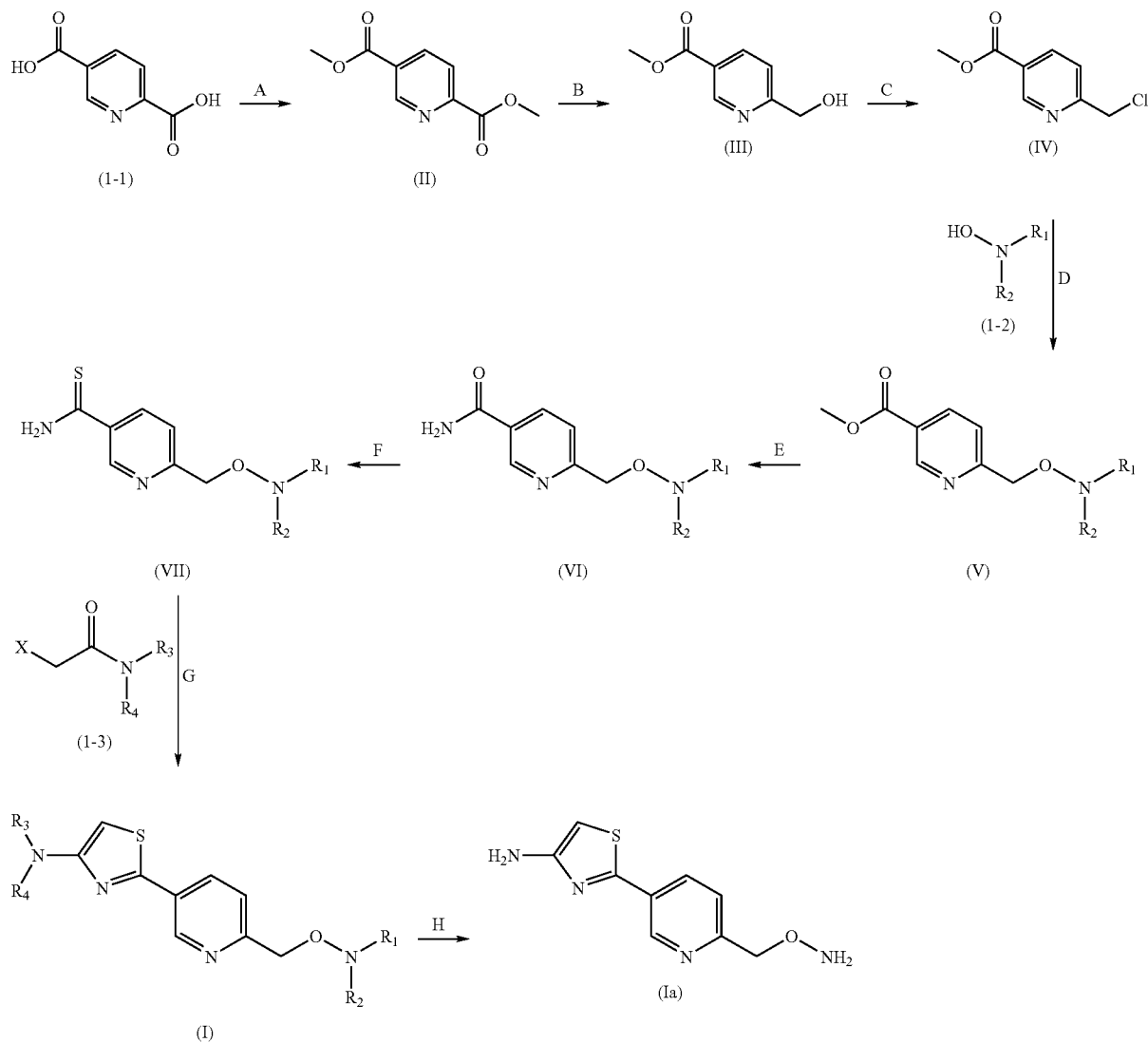

Scheme 1

A compound of formula (V) is prepared by adding a compound of formula (1-2), to a compound of formula (IV), as illustrated in Step D, wherein $R_1$ and $R_2$ are as previously defined. The present conversion preferably takes place in an aprotic solvent in the presence of a base.

As outlined in Scheme 1, Step E, a compound of Formula (VI) is prepared by reacting of compound (V) with liquid ammonia or ammonia hydroxide. In a preferred embodiment of the reaction, the reaction temperature is between 10° C. and 80° C. and the duration of the reaction is 1 to 24 hours.

As outlined in Scheme 1, Step F, a compound of Formula (VII) is prepared by reacting of compound (VI) with a thionating reagent, in organic solvent, preferably in an aprotic solvent. In a preferred embodiment of the reaction, the reaction temperature is between 10° C. and 80° C. and the duration of the reaction is 1 to 24 hours. In a particularly preferred embodiment of the reaction, the thionating reagent is phosphorus pentasulfide and the solvent is tetrahydrofuran.

As illustrated in Scheme 1, Step G, wherein $R_1$, $R_2$, $R_3$ and $R_4$ are as previously defined and X is a leaving group, a compound of formula (I) is prepared by reacting compound (VII) with a compound of formula (1-3) in organic solvent, preferably in an aprotic solvent. In a preferred embodiment of the reaction, the reaction temperature is between 20° C. and 120° C. and the duration of the reaction is 2 to 48 hours. In a particularly preferred embodiment of the reaction, the aprotic solvent is ethyl acetate.

As outlined in Scheme 1, Step H, a compound of formula (Ia) is prepared by removal of the protecting group of $R_1$, $R_2$, $R_3$ and $R_4$ in the formula (I) under either basic or acidic conditions, depending on the nature of $R_1$, $R_2$, $R_3$ and $R_4$, wherein $R_1$, $R_2$, $R_3$ and $R_4$ are as previously defined.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of dimethylpyridine-2,5-dicarboxylate (II)

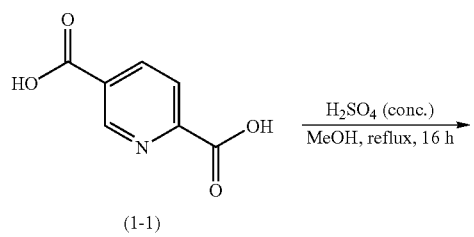

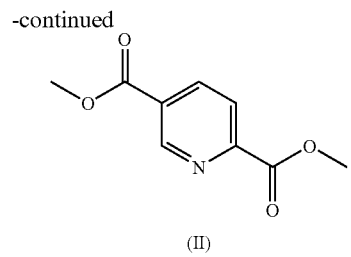

Sulfuric acid (95-98%, 22.0 ml, 1.1 eq) was added to a suspension of diacid (1-1, 60.0 g) in anhydrous methanol (600 ml) at room temperature. The resulting mixture was refluxed for 16-20 hours and then cooled to room temperature (product crystallized out). The resulting suspension was poured into a stirring mixture of saturated aqueous sodium carbonate solution (200 ml) and ice (100 g). After stirring at room temperature for 3-5 hours, the insoluble was collected by filtration, washed with water (200-300 ml), air dried overnight and then vacuum dried to afford the desired product (60.3 g, 86%) as light yellow powder. MS-ESI m/z 196.10 (M+H)$^+$; $^1$H NMR (CDCl$_3$) δ 9.31 (d, J=1.5 Hz, 1H), 8.46 (dd, J=2 and 8 Hz, 1H), 8.22 (d, J=8 Hz, 1H), 4.05 (s, 3H), 4.00 (s, 3H) ppm.

Example 2

Preparation of 6-hydroxymethyl-nicotinic acid methyl ester (III)

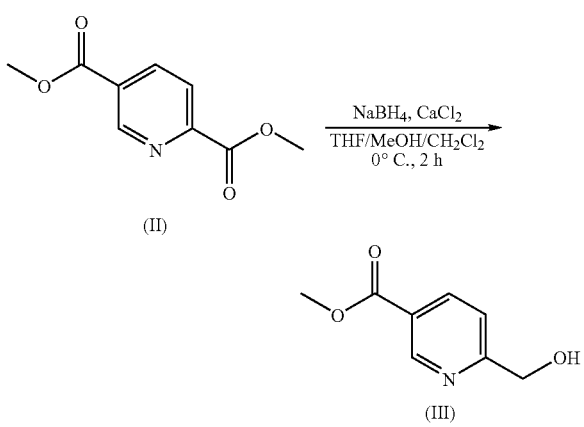

Dimethylpyridine-2,5-dicarboxylate (II, 3.6 g, 18.4 mmol) was dissolved in THF/MeOH/CH$_2$Cl$_2$ (1:2:1 v/v, 120 ml). Calcium chloride (7.0 g, 63.1 mmol, 3.4 eq) was added in one portion. The resulting clear light yellow solution was cooled to 0° C. NaBH$_4$ (0.85 g, 22.5 mmol, 1.2 eq) was added portion wise. The mixture was stirred at 0° C. for 1.5 hours, at the end of which TLC (ethyl acetate/hexanes 1:1) indicated completion of reaction. Aqueous formaldehyde (37 wt %, 4.5 g, 55.5 mmol, 3 eq) in 50 ml ice-water was added dropwise. The mixture was extracted with CHCl$_3$ (3×150 ml). The combined organic layers were dried over MgSO$_4$ and filtered. The filtrate was concentrated in vacuo and then passed through a silica gel pad (eluent 5% MeOH in CH$_2$Cl$_2$) to afford the desired product (2.95 g, 96%) as a light yellow waxy solid. MS-ESI m/z 168.12 (M+H)$^+$; $^1$H NMR (CDCl$_3$) δ 9.17 (d, J=1 Hz, 1H), 8.30 (dd, J=2 and 8.5 Hz, 1H), 7.37 (d, J=8.5 Hz, 1H), 4.84 (d, J=5 Hz, 2H), 3.96 (s, 3H), 3.63 (t, J=5 Hz, 1H) ppm.

Example 3

Preparation of 6-chloromethyl-nicotinic acid methyl ester (IV)

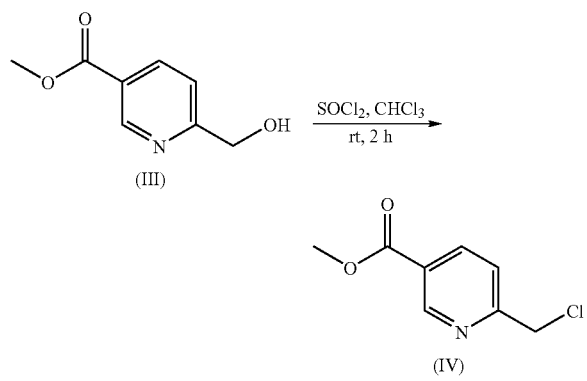

Thionyl chloride (5.0 ml, 2.0 eq) was added dropwise to a solution of alcohol (III, 5.7 g) in anhydrous chloroform (50 mL) cooling with a water bath. The resulting solution was stirred at room temperature for 2 hours. The reaction was quenched with saturated aqueous sodium bicarbonate solution followed by $CH_2Cl_2$ extractions. The combined organic layers were dried over $MgSO_4$ and filtered. The filtrate was concentrated in vacuo and then passed through a silica gel pad (eluent 5% MeOH in $CH_2Cl_2$) to afford the desired product (7.0 g, 90%) as a off-white solid. MS-ESI m/z 186.09 $(M+H)^+$; $^1H$ NMR $(CDCl_3)$ δ 9.18 (d, J=2 Hz, 1H), 8.35 (dd, J=2 and 8.5 Hz, 1H), 7.61 (d, J=8.5 Hz, 1H), 4.74 (s, 2H), 3.98 (s, 3H) ppm.

Example 4

Preparation of 6-N-Boc-aminooxymethyl-nicotinic acid methyl ester (Vb)

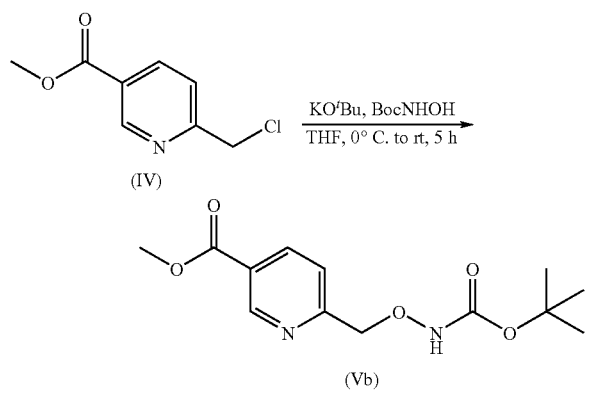

Potassium tert-butoxide (16.2 g, 140 mmol, 1.3 eq) was added to a solution of N-Boc-hydroxyamine (18.6 g, 140 mmol, 1.3 eq) in THF (300 ml) at room temperature with stirring. The mixture was cooled to 3-5° C., and then a solution of chloride (IV, 20.0 g, 107.7 mmol) in THF (50 ml) was added within 10-20 min. The reaction mixture was stirred at 3-5° C. for 1 hour and then stirred at room temperature for 5 hours. The reaction was quenched with ice-water (200 ml) followed by extraction with EtOAc (3×200 ml). The combined organic layers were washed with brine (200 ml), dried over $Na_2SO_4$ and concentrated in vacuo. The residue was vacuum dried to afford the desired product (30 g, 100%), which was used in the next step without further purification. MS-ESI m/z 283.18 $(M+H)^+$; $^1H$ NMR $(CDCl_3)$ δ 9.18 (d, J=1.5 Hz, 1H), 8.32 (dd, J=2 and 8 Hz, 1H), 7.59 (s, 1H), 7.57 (d, J=8.5 Hz, 1H), 5.08 (s, 2H), 3.96 (s, 3H), 1.48 (s, 9H) ppm.

Example 5

Preparation of 6-N-Boc-aminooxymethyl-nicotinamide (VIb)

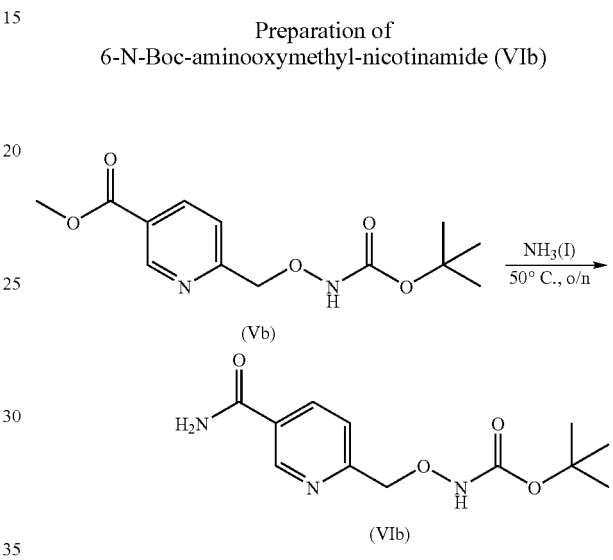

The ester (Vb, 1.23 g, 4.36 mmol) was added to liquid ammonia (5 ml) at −78° C. The reaction flask was sealed and the reaction mixture was stirred at 50° C. for 24 hours. The reaction flask was cooled down to −78° C. and opened. The reaction mixture was slowly warmed to room temperature with stirring and under a stream of nitrogen. EtOAc (15 ml) was added and the mixture was stirred for 30 min. The insoluble was collected by filtration, washed with EtOAc and vacuum dried to afford the desired amide (1.0 g, 86%) as an off-white powder. MS-ESI m/z 268.13 $(M+H)^+$; $^1H$ NMR (DMSO-$d^6$) δ 8.97 (d, J=2 Hz, 1H), 8.23 (dd, J=2 and 8 Hz, 1H), 8.15 (bs, 1H), 7.59 (d, J=8 Hz, 1H), 7.58 (bs, 1H), 4.87 (s, 2H), 1.40 (s, 9H) ppm; $^{13}C$ NMR (DMSO-$d^6$) δ 166.9, 159.8, 157.0, 148.8, 136.4, 129.5, 122.3, 80.7, 78.3, 28.7 ppm.

Example 6

Preparation of 6-N-Boc-aminooxymethyl-thionicotinamide (VIIb)

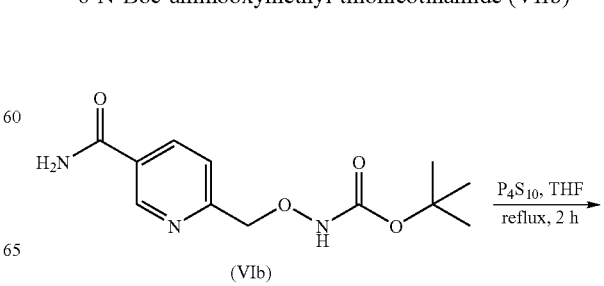

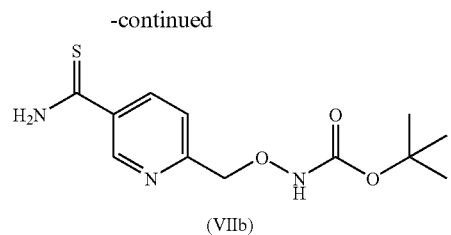

(VIIb)

The amide (VIb, 505 mg, 1.89 mmol) and P₄S₁₀ (208 mg, 0.47 mmol, 0.25 eq) were stirred in refluxing THF (15 ml) for 1 hour. Additional P₄S₁₀ (82 mg, 0.18 mmol, 0.10 eq) was added and the mixture was refluxed for another hour. The reaction mixture was cooled and filtered. The solid was washed with ethyl acetate. The combined filtrates were concentrated in vacuo and aqueous Na₂HPO₄ (500 mg in 10 ml water) solution was added to the residue. The mixture was stirred at 0° C. for 1 hour and then filtered and washed with water. The solid was dried in vacuo to afford the desired product (325 mg, 61%) as a yellow crystalline solid. MS-ESI m/z 284.16 (M+H)$^+$; $^1$H NMR (DMSO-d$^6$) δ 10.16 (bs, 1H), 10.06 (bs, 1H), 9.71 (bs, 1H), 8.95 (d, J=1 Hz, 1H), 8.23 (dd, J=2.5 and 7.5 Hz, 1H), 7.54 (d, J=8.5 Hz, 1H), 4.86 (s, 2H), 1.40 (s, 9H) ppm; $^{13}$C NMR (DMSO-d$^6$) δ 198.2, 159.5, 157.0, 147.8, 136.1, 134.9, 121.9, 80.7, 78.2, 28.7 ppm.

Example 7

Preparation of (2-bromo-acetyl)-carbamic acid tert-butyl ester (1-3b)

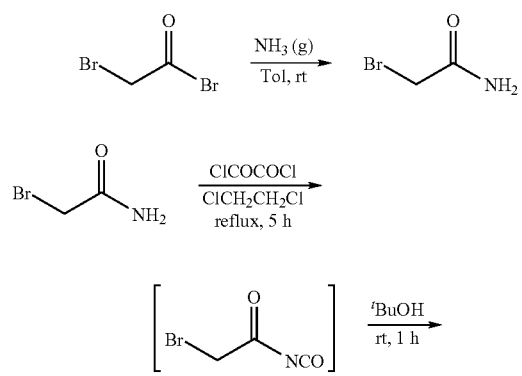

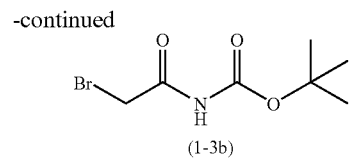

(1-3b)

2-Bromoacetylbromide (1 g, 5.0 mmol) was dissolved in toluene (8 ml). Ammonia was bubbled in at room temperature. Lots of white precipitate formed and reaction is exothermic. After the reaction was done (monitored by $^1$H NMR), the solvent was removed and the residue was triturated with methylene chloride. Removal of solvent afforded 2-bromo-actamide (0.55 g, 80%).

2-Bromoacetamide (11.1 g, 80 mmol) was suspended in ethylene dichloride (130 ml) in a 250-ml round-bottomed flask fitted with a magnetic stirrer, a thermometer, and a condenser with nitrogen flow. Oxalyl chloride (9.76 ml, 112 mmol, 1.4 eq) was added slowly to the solution at room temperature with stirring. The mixture was stirred at room temperature for 30 min, and then heated to reflux for 5 hours (the suspension became a clear solution). The condenser was replaced with a distillation system, and about 35-40 ml solvent was removed with stirring. The heating mantle was withdrawn and the reaction mixture was cooled with an ice bath to 0-5° C. A solution of tert-butanol (10.7 ml, 112 mmol, 1.4 eq) in 10 ml dichloromethane was added slowly to maintain temperature below 15° C. and the mixture was stirred at 0-15° C. for 15-30 min. The reaction mixture was diluted with dichloromethane (220 ml) and washed sequentially with aqueous saturated sodium bicarbonate solution (50 ml) and water (3×80 ml) (The amount of unreacted 2-bromoacetamide in organic layer should be controlled to <1% by $^1$H NMR or HPLC, otherwise, continue washing with water to meet this requirement). The combined organic layers were concentrated under reduced pressure to remove about 200-250 ml solvent (A slurry was formed). Heptane (110 ml) was added and the mixture was concentrated to remove about 50-70 ml solvent at reduced pressure. Heptane (110 ml) was added and the mixture was heated to 50° C. for 30 min, and then cooled to room temperature. The mixture was stirred at room temperature for 1 hour and filtered and washed with heptane (30 ml) to afford the desired product (15.5 g, 86%) as a white crystalline solid.

Example 8

Preparation of N-Boc-O-[5-(4-N-Boc-amino-thiazol-2-yl)-pyridin-2-ylmethyl]-hydroxylamine (Ib)

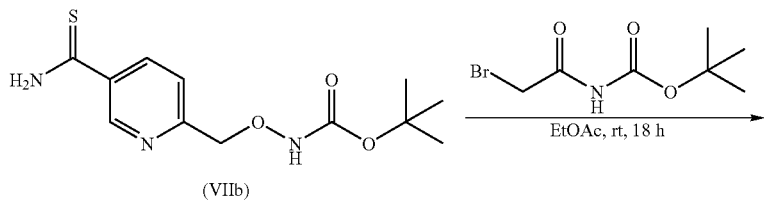

(VIIb)

-continued

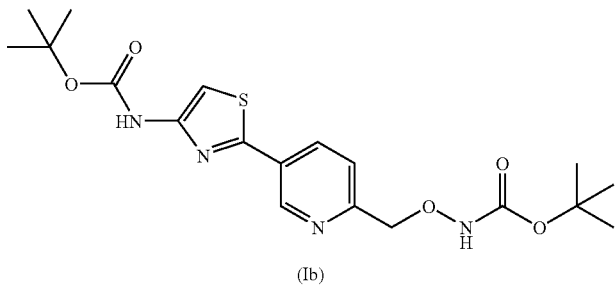

(Ib)

The thioamide (VIIb, 430 mg, 1.52 mmol) was dissolved in hot EtOAc (12 ml) and (2-bromo-acetyl)-carbamic acid tert-butyl ester (600 mg, 2.52 mmol, 1.66 eq) was added. The mixture was stirred at room temperature for 18 hours. The insoluble was collected by filtration and washed with EtOAc/hex (1:2). The solid was dissolved in $CH_2Cl_2$ (8 ml), washed with saturated aqueous sodium bicarbonate solution (8 ml), dried over $MgSO_4$ and filtered. Solvent was removed and the residue was crystallized from EtOAc/hex (1:1, 4 ml) to afford the desired product (355 mg, 55%) as an off-white crystalline solid. MS-ESI m/z 423.29 (M+H)$^+$; $^1$H NMR (CDCl$_3$) δ 9.09 (d, J=1.5 Hz, 1H), 8.14 (dd, J=2 and 8 Hz, 1H), 7.68 (bs, 1H), 7.62 (s, 1H), 7.53 (d, J=8.5 Hz, 1H), 7.32 (bs, 1H), 5.06 (s, 2H), 1.54 (s, 9H), 1.49 (s, 9H) ppm; $^{13}$C NMR (CDCl$_3$) δ 161.7, 157.9, 156.9, 152.6, 149.2, 147.0, 134.1, 128.8, 122.7, 99.3, 82.3, 78.7, 28.5, 28.4 ppm.

Example 9

Preparation of HCl salt of O-[5-(4-amino-thiazol-2-yl)-pyridin-2-ylmethyl]-hydroxylamine (Ia)

The starting material (Ib, 20 g, 47.3 mmol) was suspended in methanol (120 ml) and HCl in dioxane (4N, 70 ml, 280 mmol, 5.9 eq) was added slowly. The resulting clear solution was stirred at room temperature for 18 hours. Removal of solvent afforded the desired product as a yellow solid. MS-ESI m/z 223.11 (M+H)$^+$.

Although the invention has been described in detail with respect to various preferred embodiments it is not intended to be limited thereto, but rather those skilled in the art will recognize that variations and modifications may be made therein which are within the spirit of the invention and the scope of the appended claims.

While this invention has been particularly shown and described with references to preferred embodiments thereof, it will be understood by those skilled in the art that various changes in form and details may be made therein without departing from the scope of the invention encompassed by the appended claims.

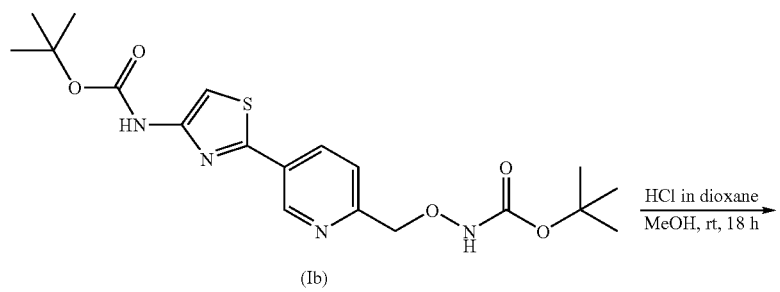

(Ib)

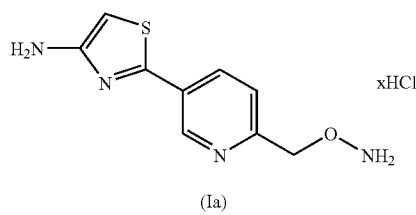

(Ia)

What is claimed:

1. A process for preparing a compound of formula (I):

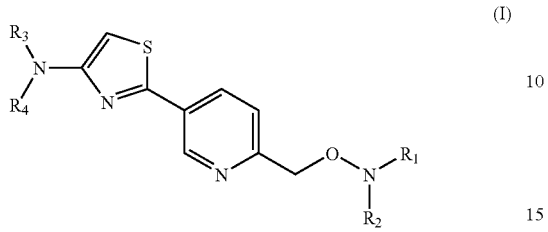

(I)

wherein $R_1$, $R_2$, $R_3$ and $R_4$ are each independently selected from:
(a) hydrogen; or
(b) $NH_2$;
or one of $R_1$ and $R_2$ and/or one of $R_3$ and $R_4$ is hydrogen and the other of $R_1$ and $R_2$ and/or the other of $R_3$ and $R_4$ is selected from:
(a) $C(O)R_5$, where $R_5$ is $C_1$-$C_6$ alkyl, optionally substituted with one or more substituents selected from aryl, substituted aryl, heteroaryl, or substituted heteroaryl;
(b) $C(O)OR_5$, where $R_5$ is as previously defined;
alternatively, $R_1$ and $R_2$ and/or $R_3$ and $R_4$ are taken together with the nitrogen atom to which they are attached to form
(a)

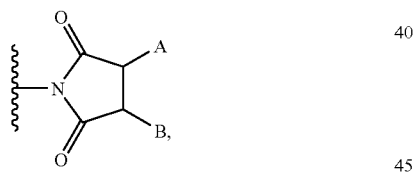

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group; or A and B taken together with the carbon to which they are attached form a cyclic moiety selected from: aryl, substituted aryl, heterocyclic, substituted heterocyclic, alicyclic, or substituted alicyclic;
b) $N=C(R_6)(R_7)$, where $R_6$ and $R_7$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;

said process comprising of the following steps:
(1) halogenating 6-hydroxymethyl-nicotinic acid methyl ester (III) with a chlorinating reagent to form a compound of formula (IV):

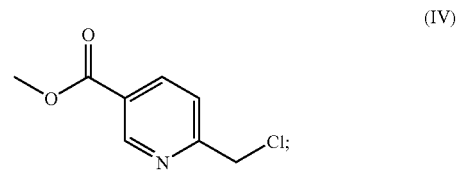

(IV)

(2) treating the compound of formula (IV) with a compound of formula $R_1R_2NOH$, wherein $R_1$ and $R_2$ are as previously defined, in the presence of base to yield a compound of formula (V):

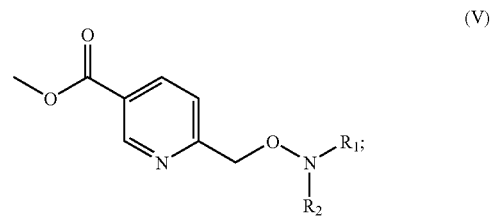

(V)

(3) reacting the compound of formula (V) with liquid ammonia or ammonium hydroxide to provide a compound of formula (VI);

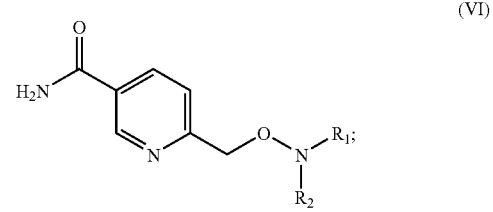

(VI)

(4) reacting the compound of formula (VI) with a thionating reagent to provide a compound of formula (VII):

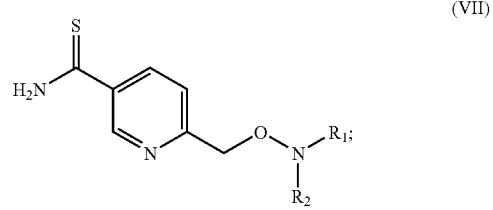

(VII)

(5) reacting the compound of formula (VII) with XCH$_2$CONR$_3$R$_4$, where X is a leaving group, to provide the compound of formula (I):

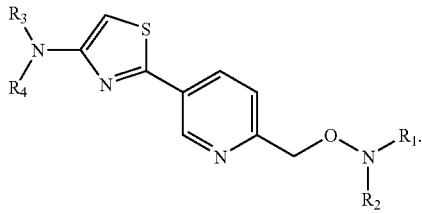

(I)

2. The process of claim 1 further comprising the step of hydrolyzing the compound of formula I with a base or an acid in a protogenic organic solvent or aqueous solution, to yield a compound of formula (Ia), O-[5-(4-amino-thiazol-2-yl)-pyridin-2-ylmethyl]-hydroxylamine, having the formulae (Ia):

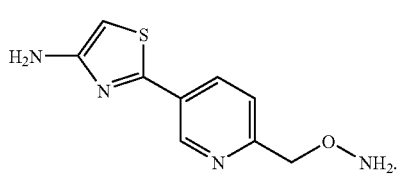

(Ia)

3. The process of claim 1, wherein step 1 comprises reacting thionyl chloride with 6-hydroxylmethyl-nicotinic acid methyl ester to provide 6-chloromethyl-nicotinic acid methyl ester.

4. The process of claim 1, wherein step 2 comprises reacting N-Boc-hydroxyamine with 6-chloromethyl-nicotinic acid methyl ester in the presence of potassium tert-butoxide to provide 6-N-Boc-6-aminooxymethyl-nicotinic acid methyl ester.

5. The process of claim 1, wherein step 3 comprises reacting 6-N-Boc-6-aminooxymethyl-nicotinic acid methyl ester in the presence of liquid ammonia to provide 6-N-Boc-aminooxymethyl-nicotinamide.

6. The process of claim 1, wherein step 4 comprises reacting phosphorus pentasulfide with 6-N-Boc-aminooxymethyl-nicotinamide to provide 6-N-Boc-aminooxymethyl-thionicotinamide.

7. The process of claim 1, wherein step 5 comprises reacting (2-bromo -acetyl)-carbamic acid tent-butyl ester with 6-N-Boc-aminooxymethyl-thionicotinamide to provide N-Boc-O-[5-(4-N-Boc-amino-thiazol-2-yl)-pyridin-2-ylmethyl]-hydroxylamine.

8. The process of claim 2, wherein the compound of Formula I is N-Boc-O -[5-(4-N-Boc-amino-thiazol-2-yl)-pyridin-2-ylmethyl]-hydroxylamine and said compound is hydrolyzed by reaction with hydrogen chloride in dioxane/methanol to provide O-[5-(4-amino-thiazol-2-yl)-pyridin-2-ylmethyl]-hydroxylamine.

9. A process for preparing a compound of formula (I):

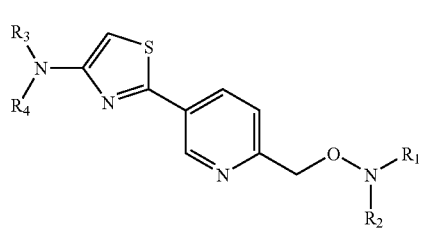

(I)

wherein R$_1$, R$_2$, R$_3$ and R$_4$ are each independently selected from:
(a) hydrogen; and
(b) NH$_2$;
or one of R$_1$ and R$_2$ and/or one of R$_3$ and R$_4$ is hydrogen and the other of R$_1$ and R$_2$ and/or the other of R$_3$ and R$_4$ is selected from:
(a) C(O)R$_5$, where R$_5$ is C$_1$-C$_6$ alkyl, optionally substituted with one or more substituents selected from aryl, substituted aryl, heteroaryl, or substituted heteroaryl; and
(b) C(O)OR$_5$, where R$_5$ is as previously defined;
alternatively, R$_1$ and R$_2$ and/or R$_3$ and R$_4$ are taken together with the nitrogen atom to which they are attached to form:
(a)

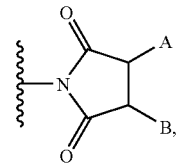

wherein A and B are each independently hydrogen, a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group; or A and B taken together with the carbon to which they are attached form a cyclic moiety selected from: aryl, substituted aryl, heterocyclic, substituted heterocyclic, alicyclic, or substituted alicyclic; and b) N=C(R$_6$)(R$_7$), where R$_6$ and R$_7$ are each independently selected from a substituted or unsubstituted aliphatic group, a substituted or unsubstituted cyclic group, a substituted or unsubstituted heterocyclic group, a substituted or unsubstituted aryl group, a substituted or unsubstituted alicyclic group, or a substituted or unsubstituted heteroaryl group;

said process comprising the step of:
reacting a compound of formula (VII):

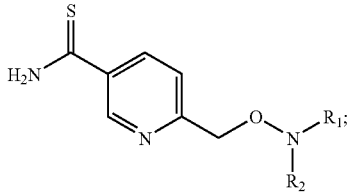
(VII)

with XCH$_2$CONR$_3$R$_4$, where X is a leaving group, to provide the compound of formula (I):

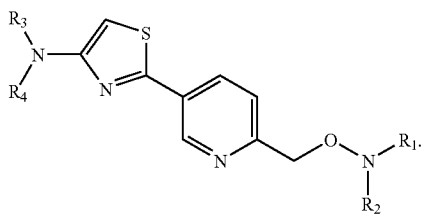
(I)

10. The process of claim 9, wherein:
(a) the compound of formula (VII) is 6-N-Boc-aminooxymethyl-thionicotinamide;
(b) XCH$_2$CONR$_3$R$_4$ is (2-bromo-acetyl)-carbamic acid tert-butyl ester; and
(c) the compound of formula (I) is N-Boc-O-[5-(4-N-Boc-amino-thiazol-2-yl)-pyridin-2-ylmethyl]-hydroxylamine.

11. The process of claim 9 further comprising the step of hydrolyzing the compound of formula I with a base or an acid in a protogenic organic solvent or aqueous solution, to yield a compound of formula (Ia), O-[5-(4-amino-thiazol-2-yl)-pyridin-2-ylmethyl]-hydroxylamine, having the formulae (Ia):

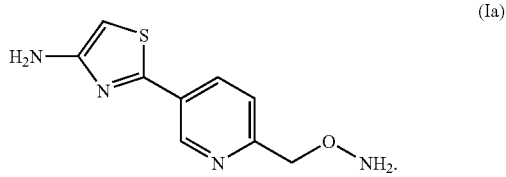
(Ia)

12. The process of claim 11, wherein the compound of Formula I is N-Boc-O-[5-(4-N-Boc-amino-thiazol-2-yl)-pyridin-2-ylmethyl]-hydroxylamine and said compound is hydrolyzed by reaction with hydrogen chloride in dioxane/methanol to provide O-[5-(4-amino-thiazol-2-yl)-pyridin-2-ylmethyl]-hydroxylamine.

* * * * *

UNITED STATES PATENT AND TRADEMARK OFFICE
CERTIFICATE OF CORRECTION

| | | |
|---|---|---|
| PATENT NO. | : 7,842,813 B2 | Page 1 of 1 |
| APPLICATION NO. | : 12/437636 | |
| DATED | : November 30, 2010 | |
| INVENTOR(S) | : Datong Tang et al. | |

It is certified that error appears in the above-identified patent and that said Letters Patent is hereby corrected as shown below:

Column 25

At Claim 7, line 56, delete "tent-butyl" and insert -- tert-butyl --.

Signed and Sealed this
First Day of March, 2011

David J. Kappos
*Director of the United States Patent and Trademark Office*